(12) United States Patent
Stevens

(10) Patent No.: US 6,410,692 B2
(45) Date of Patent: Jun. 25, 2002

(54) REMOVAL OF ABUNDANT INTERFERING PROTEINS FROM A LIQUID SAMPLE USING A COLLAPSIBLE AFFINITY MATRIX

(75) Inventor: Anthony C. Stevens, San Diego, CA (US)

(73) Assignee: NovaDx, Inc., San Diego, CA (US)

( * ) Notice: Subject to any disclaimer, the term of this patent is extended or adjusted under 35 U.S.C. 154(b) by 0 days.

(21) Appl. No.: 09/017,284

(22) Filed: Feb. 2, 1998

(51) Int. Cl.$^7$ .............................................. C07K 16/00
(52) U.S. Cl. ............... 530/388.25; 530/363; 530/388.1; 436/548; 436/541; 436/516; 436/525; 422/61
(58) Field of Search .................................. 436/516, 541, 436/525, 548; 210/198.2; 424/485; 204/459; 435/5, 240.25; 530/388.1, 363, 388.25; 422/61

(56) References Cited

U.S. PATENT DOCUMENTS

| | | | | |
|---|---|---|---|---|
| 4,444,879 A | * | 4/1984 | Foster et al. .................... | 435/7 |
| 4,521,522 A | * | 6/1985 | Lundstrom et al. .......... | 436/525 |
| 4,727,023 A | * | 2/1988 | Wang et al. ..................... | 435/7 |
| 4,735,898 A | * | 4/1988 | Herr et al. ....................... | 435/7 |
| 4,737,456 A | * | 4/1988 | Weng et al. ..................... | 435/7 |
| 4,837,170 A | * | 6/1989 | Ohe et al. .................... | 436/548 |
| 5,112,770 A | * | 5/1992 | Carbonell et al. ........... | 436/501 |
| 5,167,925 A | * | 12/1992 | Carbonell et al. ............. | 422/61 |
| 5,212,063 A | * | 5/1993 | Ofenloch-Hahnle et al. . | 435/7.5 |
| 5,240,602 A | * | 8/1993 | Hammen .................. | 210/198.2 |
| 5,262,334 A | * | 11/1993 | Berenson et al. ............ | 436/541 |
| 5,277,915 A | * | 1/1994 | Provonchee et al. ......... | 424/485 |
| 5,280,078 A | * | 1/1994 | Gregor et al. ............ | 525/328.5 |
| 5,472,867 A | * | 12/1995 | Kanz et al. ............. | 435/240.25 |
| 5,534,121 A | | 7/1996 | Merrick et al. .............. | 204/459 |
| 5,616,690 A | * | 4/1997 | Axworthy et al. ........... | 530/363 |
| 5,643,731 A | * | 7/1997 | Bosslet et al. ................ | 435/7.1 |
| 5,650,333 A | * | 7/1997 | Holtlund ...................... | 436/525 |
| 5,736,317 A | * | 4/1998 | Sarngadharan et al. ......... | 435/5 |
| 5,863,740 A | * | 1/1999 | Kientsch-Engel et al. ... | 435/7.5 |
| 5,888,745 A | * | 3/1999 | Eckert et al. ................. | 435/7.1 |
| 5,952,185 A | * | 9/1999 | Huber et al. .................. | 435/7.5 |

OTHER PUBLICATIONS

Benjamin, DC et al, Hybridoma, Apr. 1987, vol. 6(2), pp. 183–190.*
Diamandis, EP et al, Annals of Clinical Biochemistry, May 1990, vol. 27(part 3), pp. 232–237.*
Doyen, N et al, Molecular Immunology, vol. 22(1), pp. 1–10, Jan. 1985 (abstract only).*
Lapresle, C et al, Molecular Immunology, vol. 20(5), pp. 549–555, May 1983.*
Zaman et al, Journal of Automatic Chemistry, vol. 15(6), pp. 189–208, Nov.–Dec. 1993.*
Remington, K. et al, Fed. Am. Soc. Exp. Biol, vol. 3(4), p. A1131, Abstract #5255, 1989.*
Phillips, T.M., Clin. Chem, vol. 34(9), p. 1689–1692, 1988.*
Gretcht, DR et al, Anal. Biochem., May 15, 1987, vol. 163(1), p 270–277.*
Hall, TM et al, Ann. N.Y. Acad. Sci., Sep. 7, 1994, vol. 731, p 115–127.*
Wojchowski, D.M et al, Biochem Biophys Acta, (abstract) May 9, 1986, vol. 857(1), p 61–67.*
Ledden, D.J. et al, J. Protein Chem,, vol. 2(4), p 303–319, 1983.*
Latta, M. et al, Biotechnology, vol. 5, Dec., 1987, p 1309–1314.*
Andersson, I et al, Vox Sanguinis, vol. 70 (Suppl 2), p 120, Abstract #1/2E–370p, 1996.*
Updyke, T.V. et al, Immunolog., Methods, vol. 73, p 83–95, 1984.*
Wilchek, M et al, Anal. Biochem., vol. 171, p 1–32, 1988.*
Li et al, Dyes and Pigments, vol. 22, No. 1, p 27–45, 1993.*
Wojchowski, D.M. et al, J. Immunol. Methods, Jun. 24, 1986, (abstract) vol. 90(2), p 173–177.*
Rabilloud et al. "Sample application by in–gel rehydration improves the resolution of two–dimensional electrophoresis with immobilized pH gradients in the first dimension," *Electrophoresis* 15: 1552–1558 (1994).

* cited by examiner

*Primary Examiner*—Lynette R. F. Smith
*Assistant Examiner*—Ginny Allen Portner
(74) *Attorney, Agent, or Firm*—Fish & Richardson P.C.

(57) ABSTRACT

A method for specifically immunoprecipitating albumin from a serum sample, using a "collapsible affinity matrix." Also provided is a method for the co-removal of immunoglobulin using a "collapsible affinity matrix." Removal of the highly abundant serum proteins, albumin and immunoglobulin, thereby improves the fractionation of the remaining serum proteins. Due to the collapsible nature of the matrix, less protein is trapped in the void space. Through specific removal of the abundant serum proteins by the collapsible affinity matrix and application of a two dimensional gel electrophoresis method, HiCap 2-D PAGE, the concentrations of a large number of low abundant serum proteins are estimated simultaneously, allowing the identification of several disease-related proteins in a relatively short period of time.

9 Claims, 14 Drawing Sheets

REMOVAL OF ABUNDANT INTERFERING PROTEINS FROM A LIQUID SAMPLE USING A COLLAPSIBLE AFFINITY MATRIX

BACKGROUND OF THE INVENTION

Since the development of high resolution two-dimensional (2-D) electrophoresis by O'Farrell, the technique has been applied to mapping the protein composition of human serum and of various tissues. 2-D electrophoresis consists of isoelectric focusing electrophoresis (IEF) in the first dimension and SDS polyacrylamide gel electrophoresis [SDS-PAGE] in the second dimension. Current interest in using 2-D electrophoresis to identify disease related proteins is exemplified by the existence of databases dedicated to 2-D polypeptide maps of serum and tissue samples of different disease states.

Although 2-D electrophoresis is considered to be the most powerful separation technique for resolving highly complex protein mixtures, the method has limitations. Most of these limitations are related to sample composition, such as high concentrations of salt and protein. The advent of immobilized pH gradient (IPG) strips has greatly minimized these limitations. Even when using immobilized pH gradient strips, however, suggested sample loadings of human serum are on the same order of magnitude (1–5 $\mu$L) as that used with the "classical" O'Farrell technique for analytical 2-D electrophoresis.

The limitation of human serum sample volume is due to the protein distribution and not necessarily the total protein, although total protein is a significant limitation with the O'Farrell technique. A single protein, albumin (HSA), makes up approximately 50% of the total human serum protein. This protein can distort the gel image of a 2-D protein map when large sample volumes are used. The limitation in sample volume ultimately limits the number of proteins that can be detected by 2-D electrophoresis.

The distortion in the gel image is particularly evident in the area of the albumin (molecular weight [MW] 66,000, pI 4.9) where vertical and horizontal streaking masks a large portion of the protein map. In addition, a group of abundant serum proteins, immunoglobulin (Ig), contributes approximately 20% to total human serum protein. Vertical and horizontal streaking also masks the portion of the protein map in the area of the gel image where Ig light and heavy chains are located. Furthermore, the presence of the abundant HSA and Ig alters the pI of the isoelectric focusing electrophoresis gel in these proteins, impeding effective resolution and detection of many other protein spots. To improve 2-D electrophoresis human serum maps, in both quality of image and the number of detectable proteins, human serum albumin must be specifically removed.

There are currently several methods for removing albumin from serum, such as adsorption to activated carbon particles, binding to Cibacron-blue dye coupled to Sepharose beads, and the use of anti-albumin polyclonal antibodies. Removal of serum albumin using carbon or the Cibacron-blue Sepharose is relatively inexpensive, but these methods suffer from a lack of specificity. The Cibacron-blue dye binds many proteins other than albumin, such as interferon, lipoproteins, blood coagulation factors, kinases, dehydrogenases and most enzymes requiring adenyl-containing cofactors. Also, because of the microporous nature of the Sepharose beads, additional proteins are trapped in the dead volume of the rigid matrix.

SUMMARY OF THE INVENTION

The present invention provides a method for removing interfering macromolecules from a liquid sample before protein fractionation. This method involves contacting the liquid sample with a polypeptide affinity reagent that has specificity for an abundant macromolecule in the sample, and is one member of a high affinity binding pair system. A macromolecule-polypeptide affinity reagent complex is formed, that is then contacted with the other member of a high affinity binding pair system to form a "collapsible affinity matrix." The collapsible affinity matrix is specific for the abundant macromolecule and, when centrifuged, contains very little dead volume that would otherwise trap additional sample macromolecules. In one embodiment, the invention provides a method for specifically removing macromolecules from a sample using biotinylated adsorptive proteins. In a specific embodiment, a biotinylated anti-HSA antibody, in conjunction with avidin and human serum, forms a collapsible affinity matrix, containing albumin. The combination of biotinylated protein A, avidin, and human serum, followed by contact with biotinylated anti-HSA and avidin allows simultaneous co-precipitation of albumin and immunoglobulin (Ig). The practice of the method of the invention can thereby provide serum samples substantially depleted of albumin and immunoglobulin.

The invention also provides a monoclonal antibody (HSA2126NX.012) that can specifically immunoprecipitate albumin from serum. The invention further provides a kit useful for specifically removing abundant macromolecules from a sample using biotinylated adsorptive proteins.

This unique method for removing albumin and immunoglobulin from serum permits the full potential of the powerful protein fractionation technique of high resolution 2-D electrophoresis to be attained, by making possible visualization of low abundant serum proteins, as well as those proteins that would normally be obscured by the serum albumin and immunoglobulin. This advantage allows for identification and characterization of a variety of novel markers that may have diagnostic or therapeutic utility. For example, the discovery of novel biochemical serum markers for the diagnosis of various disease states such as osteoporosis, arthritis, cancer or cardiovascular disease can aid immensely in the management of these conditions.

The removal of high abundant macromolecules from a liquid sample followed by a high resolution 2-D electrophoresis allows for visualization of low abundant sample proteins that might not be visualized with limits in total protein load. When the high resolution 2-D electrophoresis includes in-gel sample rehydration of immobilized pH gradient strips, followed by isoelectric focusing in the first dimension and SDS-PAGE in the second dimension, this method is called "High Capacity Two-Dimensional Polyacrylamide Gel Electrophoresis" ("HiCap 2-D PAGE"). HiCap 2-D PAGE permits relatively high amounts of low abundant proteins to be loaded following the removal of albumin and immunoglobulin. HiCap 2-D PAGE also permits the use of large sample load due to in-gel sample rehydration. The combination of abundant serum protein removal by the collapsible affinity matrix and HiCap 2-D PAGE produces highly reproducible maps of low abundance serum proteins in human serum.

DESCRIPTION OF THE DRAWINGS

FIG. 5 shows normalized intensity of 18 paired spots from gel 1 (see, FIG. 4A) and gel 2 (see, FIG. 4B). FIG. 5 represents the reproducibility of HiCap 2-D PAGE from a quantitative point of view. Two identical 100 μL human serum samples were treated and analyzed using HiCap 2-D PAGE according to the methods described in EXAMPLES III and IV. Eighteen paired spots were randomly chosen and the individual normalized densities (NOD) between the two gels were compared. The average variation in NOD between the duplicate gels was about 25%.

FIG. 6A shows spot ID 118 concentration (2-D PAGE) and NTx concentration (commercial assay) in the serum of a Paget's disease patient over time.

FIG. 7A is the collapsible affinity matrix sample.

DETAILED DESCRIPTION OF THE INVENTION

Figure 1A:
FIGS. 1A–C are a 2-D PAGE of 5 $\mu$L human serum, where the serum is A) untreated; B) treated with anti-HSA monoclonal HSA2126NX.012; and C) treated with Cibacron-blue.

The present invention provides a method for removing interfering macromolecules from a liquid sample before protein fractionation. The liquid sample is contacted with a polypeptide affinity reagent having specificity for an abundant macromolecule in the sample. The polypeptide affinity reagent is one member of a high affinity binding pair system, and contacting the sample with the polypeptide affinity reagent forms a macromolecule-polypeptide affinity reagent complex. Then, the macromolecule-polypeptide affinity reagent complex is contacted with a second member of a high affinity binding pair system to form a "collapsible affinity matrix." The collapsible affinity matrix is a stable aggregation of the macromolecule-polypeptide affinity reagent complexes.

In one embodiment, the invention provides a method for specifically removing macromolecules from a liquid sample using biotinylated adsorptive proteins and a second member of the high affinity binding pair system, such as avidin, streptavidin, or NEUTRAVIDIN™ (Molecular Probes, Inc., Eugene, Oreg.). For example, albumin can be specifically removed from a serum sample using biotinylated anti-human serum albumin monoclonal antibody, with avidin, streptavidin, or NEUTRAVIDIN™. The invention thus provides a serum sample substantially depleted in albumin and immunoglobulin.

The invention further provides a kit useful in the practice of the methods of the invention. The kit has two or more containers. A first container contains a monoclonal antibody that can immunoprecipitate albumin from serum, to which is bound a first member of a high affinity binding pair, for example biotin. A second container contains a second member of a high affinity binding pair, for example, avidin, streptavidin, or NEUTRAVIDIN™ (Molecular Probes, Inc. Eugene, Oreg.).

Liquid Sample

The invention provides a method for preparing a liquid sample for fractionation. As used herein, the term "sample" includes material derived from a mammalian subject, e.g., human. As well as non-mammalian animals. Such samples include but are not limited to hair, skin samples, tissue samples, cultured cells, cultured cell media, and biological fluids. The term "tissue" refers to a mass of connected cells (e.g., CNS tissue, neural tissue, or eye tissue) derived from an animal or human subject, and includes the connecting material and the liquid material in association with the cells. As used herein, the term "liquid sample" refers to liquid material derived from a human, animal, or the cells derived therefrom. Such liquid samples include but are not limited to blood, plasma, serum, serum derivatives, bile, phlegm, saliva, sweat, amniotic fluid, and cerebrospinal fluid (CSF), such as lumbar or ventricular CSF. As used herein, the term "liquid sample" also includes solutions containing an isolated macromolecule, media into which the macromolecule has been secreted, and media containing cells that produce a macromolecule of interest. For example, a liquid sample may be a protein sample that is to be resolved by SDS-PAGE and transferred to nitrocellulose for Western immunoblot analysis. The quantity of sample required for the protein fractionation can be determined by one skilled in the art by standard laboratory techniques. The optimal quantity of sample may be determined by serial dilution.

Polypeptide Affinity Reagent

The invention provides a method for preparing a liquid sample for fractionation, by contacting the liquid sample with a polypeptide affinity reagent. As used herein, the terms "polypeptide affinity reagent" refers to a polypeptide that specifically binds to a macromolecule of interest in a liquid sample to be fractionated. "Specifically binds" means the adsorptive protein recognizes and binds a specified macromolecule, but does not substantially recognize and bind other molecules in a sample, e.g., a liquid biological sample, that naturally includes a variety of macromolecules. The principle is to contact the liquid sample with reagents having specific affinity for a particular component. These reagents have narrow specificities for particular sets of macromolecules.

Antibodies represent the main class of polypeptide affinity reagents that are immunoreactive or bind to epitopes of macromolecules. The term "epitope" refers to any antigenic determinant on an antigen to which an antibody binds. Epitopes usually are chemically active surface groupings of molecules such as amino acids or sugar side chains and usually have specific three dimensional structural characteristics, as well as specific charge characteristics.

As used herein, the term "antibody" includes intact antibody molecules as well as fragments thereof, such as Fab, Fab', F(ab')$_2$, Fv, and single chain antibody that can bind the epitope. These antibody fragments retain some ability selectively to bind with corresponding antigen or receptor. Particularly useful antibodies include polyclonal and monoclonal antibodies, chimeric antibodies, single chain antibodies and the like, having the ability to bind with high immunospecificity to abundant macromolecules. These antibodies can be unlabeled or suitably labeled.

The preparation of polyclonal antibodies is well-known to those skilled in the art. See, for example, Green et al. ("Production of Polyclonal Antisera", in *Immunochemical Protocols*, Manson, ed., Humana Press, 1992, pages 1–5) and Colligan et al. (Production of Polyclonal Antisera in Rabbits, Rats, Mice and Hamsters, in: *Current Protocols in Immunology*, section 2.4.1, 1992), incorporated herein by reference.

The preparation of monoclonal antibodies likewise is conventional. Monoclonal antibodies can be produced using methods well known in the art. See, Kohler et al. (*Nature* 256: 495, 1975); *Current Protocols in Molecular Biology* (Ausubel et al., ed., 1989); and Harlow and Lane (*Antibodies: A Laboratory Manual*, Cold Spring Harbor Laboratory, New York, current edition), incorporated herein by reference. Briefly, monoclonal antibodies can be obtained by injecting mice with an antigenic composition, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with protein-A Sepharose, size-exclusion chromatography, and ion-exchange chromatography. In EXAMPLE I, HSA2126NX.012 cell culture supernatant was run over a Protein A Sepharose column.

Methods of in vitro and in vivo multiplication of monoclonal antibodies are well known to those skilled in the art. Multiplication in vitro may be carried out in suitable culture media such as Dulbecco's Modified Eagle Medium (DMEM) or RPMI 1640 medium, optionally replenished by a mammalian serum such as fetal calf serum or trace elements and growth-sustaining supplements such as normal mouse peritoneal exudate cells, spleen cells, bone marrow macrophages. In Example I, monoclonal antibody HSA2126NX.012 was produced from hybridoma (ATCC accession No. HB12464) cultures grown in medium that is serum free, contains no albumin and is low in total protein content. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. In Example I, for larger scale production, an artificial capillary system was used, where well-established bioreactor culture yields 1–3 mg antibody per mL of supernatant. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

If desired, polyclonal or monoclonal antibodies can be further purified, for example, by binding to and elution from a matrix to which the polypeptide or a peptide to which the antibodies were raised is bound. A purified antibody may be obtained, for example, by affinity chromatography using recombinantly-produced protein or conserved motif peptides and standard techniques. Those of skill in the art will know of various techniques common in the immunology arts for purification or concentration of polyclonal antibodies, as well as monoclonal antibodies. See, e.g., Colligan, et al. (Unit 9, *Current Protocols in Immunology*, Wiley Interscience, 1997).

As used herein, the term "albumin-specific monoclonal antibodies" refers to monoclonal antibodies that specifically bind to serum albumin. "Specifically binds to albumin" means the monoclonal antibody recognizes and binds to serum albumin, but does not substantially recognize and bind other molecules in a sample, e.g., serum, that naturally includes serum albumin. The invention provides a monoclonal antibody that can immunoprecipitate serum albumin from serum. This means that the monoclonal antibody recognizes an epitope on the HSA molecule that is not blocked by the numerous serum proteins that bind to HSA in serum. Thus, a monoclonal antibody, specific for HSA, can be used in an improved method for the removal of albumin from human serum. 2-D electrophoresis of human serum treated in this way is therefore improved in both the quality of image produced and the number of proteins detected. In a specific embodiment, the monoclonal antibody is HSA2126NX.012. A method for making monoclonal antibody HSA2126NX.012 is provided in EXAMPLE I.

Although polyclonal antibodies against HSA provide specificity, there is the inherent variability in antibody population that occurs during separate immunization schedules that can lead to reproducibility problems. Additionally, the supply of polyclonal antibody containing serum is limited by the health and finite lifespan of the producing animal. Considering the large quantities of anti-HSA antibody required for the treatment of serum, the use of polyclonal antibodies is possible but not preferred.

Other polypeptide affinity reagents include protein A and protein G. As used herein, "protein A" is a protein of MW 42,000 from the bacterium *Staphylococcus aureus* that binds to IgG from a wide range of species, including human, rabbit, donkey, pig, and guinea-pig. Protein A is commonly used as a secondary reagent in immunological and biological techniques, as described by Goding (*J. Immunol. Meth.* 20. 241–253, 1978), and is commercially available. In EXAMPLE II, recombinant protein A was obtained from Scripps Laboratories. As used herein, "protein G" is a monomeric protein (MW 63,000) from human group G streptococcus. Protein G possess two or three antibody-binding sites and binds IgG from a wide range of species. Compared to protein A, protein G binds with a higher affinity to rat, mouse and goat IgG, as described by Bjrk et al. (*J Immunol.* 133, 969–974, 1984).

Other polypeptide affinity reagents include lectins, which specifically bind sugars (saccharides). The definition adopted by the Nomenclature Committee of the International Union of Biochemistry states that "a lectin is a sugar-binding protein of non-immune origin that agglutinates cells or precipitates glycoconjugates." This definition provides positive and easily testable properties for identifying possible lectins. The sugar-binding property is the predominant feature of lectins and is responsible for their biological actions and their value in biological experimental techniques. Sugar-binding, in conjunction with the related agglutination action, serves to identify lectins in tissue extracts and facilitates their subsequent isolation. Although binding to red blood cells has traditionally been the way of distinguishing lectins, a few lectins do not agglutinate red blood cells. Thus, although the original definition of lectin specified the agglutination of red blood cells, the term now incorporates those proteins that agglutinate other cells, as well as some proteins that are not known at present to agglutinate any cells at all, but do bind sugars and have stretches of amino-acid sequence in their polypeptide subunits that are similar to those of more characteristic lectins. Individual lectins are usually named after the organism, in most cases a plant, from which they were obtained. Examples of individual lectins include wheat-germ agglutinin, concanavalin A from the jack-bean, and pea, lentil, and potato lectins.

Lectins are distinguished from the numerous immunoproteins and enzymes that may also bind sugars, although some lectins may have glycosidase activity.

Lectins usually consist of two or four identical polypeptide subunits. When differences between the subunits are found, however, they can be quite marked. There is usually one sugar-binding site per subunit and these sugar-binding sites are normally for the same sugar, are all of the same type, and do not interact with each other. Lectins composed of different subunits can be found in different forms (isolectins) arising from various combinations of the monomers in the complete dimer or tetramer. Subunits may differ in their amino acid sequences and, if the lectin is a glycoprotein, the subunits may also differ in the nature and linkages of the sugars in the attached oligosaccharide side chains.

The properties of lectins make them extremely important components of many techniques in cell biology and biochemistry. They are used extensively, for example, in the procedures for glycoprotein isolation, as described by Lis & Sharon ("Lectins as molecules and tools." *Annu. Rev. Biochem.* 55: 35–67, 1986).

Other polypeptide affinity reagents include DNA-binding proteins. As used herein, the term "DNA-binding proteins" refers to proteins that bind to DNA, including gene regulatory proteins, enzymes involved in DNA replication, recombination, repair, transcription, and degradation, and proteins involved in maintaining chromosome structure. They can be divided into two large groups: (1) Those that have some sequence-specific or secondary structure-specific requirement for DNA-binding, and (2) those that bind DNA nonspecifically. Examples of sequence-specific DNA-binding include homeodomain proteins; proteins involved in protein-nucleic acid interactions during recombination; restriction enzymes; and transcription factors. Examples of sequence-nonspecific DNA-binding include chromatin; proteins involved in DNA repair and DNA replication; and nucleases.

The method of the invention can be performed multiple times on a single liquid sample to remove multiple abundant molecules. For example, in EXAMPLES III and VI, the multiple abundant molecules removed from serum are albumin and immunoglobulin.

Abundant Macromolecules

The invention provides a method for preparing a liquid sample for fractionation, by contacting the liquid sample with a polypeptide affinity reagent having specificity for an abundant macromolecule in the sample. As used herein, a "macromolecule" is a molecule with a molecular weight in excess of 1,000 kilodaltons (kDa). Examples of macromolecules include polynucleotides, polypeptides, and polysaccharides. Examples also include glycoproteins, in which saccharide (sugar) moieties are covalently bound to polypeptides, and nucleoproteins, which are complexes of polynucleotide and polypeptide. The terms "albumin" and "serum albumin" refer to the most abundant of the serum proteins. In one embodiment, the serum albumin is human serum albumin (HSA). In another embodiment, described in EXAMPLE XI, serum albumin is monkey serum albumin (MSA).

An "abundant macromolecule" is a macromolecule present in a sample in such quantity that the presence of the macromolecule interferes with an aspect of the analysis of the sample. For example, a single protein, serum albumin, makes up over 50% of the total protein in human serum. This can have deleterious effects on 2-D protein maps prepared with large sample volumes, by distorting the gel image. The distortion in the gel image is particularly evident in the area of the albumin where vertical and horizontal streaking can mask a large portion of the protein map. The limitation in sample volume ultimately limits the number of other proteins that can be detected by 2-D electrophoresis.

High Affinity Binding Pair System

The invention provides a method for preparing a liquid sample for fractionation, by contacting the liquid sample with a polypeptide affinity reagent having specificity for an abundant macromolecule in the sample. The polypeptide affinity reagent is one member of a high affinity pair system. As used herein, a "high affinity binding pair system" is a pair of reagents where a first member of the high affinity binding pair system binds to the second member of the high affinity binding pair system with a functional affinity (or avidity) sufficiently strong to allow stable aggregation of the macromolecule-polypeptide affinity reagent complexes in the liquid sample under physiological conditions over the length of time that the method of the invention is practiced. A high affinity binding pair system typically exhibits an affinity between the first and second members of the high affinity binding pair of at least about $K\sim10^{-10}$. Specifically excluded from the definition of high affinity binding pair systems are antibody-second antibody systems and antibody systems that comprise complement, protein A, protein G, or Fc receptors.

In one embodiment, the high affinity binding pair system is the avidin and biotin system. Avidin binds to biotin almost irreversibly, with a dissociation constant of $K\sim10^{-15}$ M. As used herein, "avidin" is a tetrameric glycoprotein from egg white that binds to biotin. In another embodiment, the high affinity binding pair system is streptavidin and biotin. As used herein, "streptavidin" is a tetrameric protein from the prokaryote *Streptomyces avidinii* that, like avidin, binds to biotin. In another embodiment, the high affinity binding pair system is NEUTRAVIDIN™ (Molecular Probes, Inc., Eugene, Oreg.) and biotin. NEUTRAVIDIN™ is an avidin protein that has been processed to remove the carbohydrate and lower its isoelectric point. The methods used to deglycosylate the avidin retain both its specific binding and its complement of amine-conjugation sites.

The polypeptide affinity reagent is linked to a first member of a high affinity binding pair. The polypeptide affinity reagent may be linked either directly to a first member of the high affinity binding pair (i.e., the polypeptide affinity reagent and the first member of the high affinity binding pair constitute the same polypeptide) or covalently bound to a first member of the high affinity binding pair. Biotin can be covalently linked to proteins; the proteins can then be cross-linked using avidin, streptavidin, or NEUTRAVIDIN™. As used herein, the term "biotinylation" refers to the methods by which biotin can be linked covalently to polypeptides for use as a label. Use of this technique is well known in the art for localization of biotinylated primary reagents such as antibodies, lectins or cDNA, and localization of proteins that have been applied to living cells before processing, such as endocytosed ligands. Biotinylation is commonly used as an alternative method to radioactivity for labeling polypeptide. EXAMPLE II provides a description of one method of both the biotinylation of antibody and the biotinylation of protein A.

In another embodiment, the high affinity binding pair system is a hapten, such as dinitrophenol, pyridoxal, or fluorescein, and a specific anti-hapten antibody.

Collapsible Affinity Matrix

The polypeptide affinity reagent is one member of a high affinity binding pair system, and contacting the sample with the polypeptide affinity reagent forms a macromolecule-polypeptide affinity reagent complex. Then, the macromolecule-polypeptide affinity reagent complex is contacted with a second member of a high affinity binding pair system to form a collapsible affinity matrix. As used herein, a "collapsible affinity matrix" is a stable aggregation of the macromolecule-polypeptide affinity reagent complexes in the liquid sample. A collapsible affinity matrix is stable under physiological conditions over the length of time that the method of the invention is practiced. In EXAMPLE III, a collapsible affinity matrix specific for HSA and Ig was prepared by precipitating biotinylated anti-HSA bound to HSA and biotinylated protein A bound to Ig (i.e, macromolecule-polypeptide affinity reagent complexes) with avidin, the second member of the avidin/biotin high affinity binding pair system.

An advantage of the collapsible affinity matrix for protein removal is that when the matrix is pelleted by centrifugation, a low void volume pellet is formed. The collapsible nature of this novel collapsible affinity matrix is therefore superior to existing methods that use coated Sepharose beads. The collapsible affinity matrix contains less "dead" space and therefore traps less low abundant and potentially interesting protein, due to the low-volume void space, than does a rigid, microporous immobilized matrix.

The collapsible affinity matrix can be removed from the liquid sample by means known to those of skill in the art. For example, the collapsible affinity matrix can be removed by centrifugation. For another example, the collapsible affinity matrix can be removed by filtration.

Serum Substantially Depleted in Serum Albumin and Immunoglobulins

The invention thus provides a serum substantially depleted in albumin and immunoglobulins. As used herein, the term "substantially depleted" means that the serum sample, after the collapsible affinity matrix is removed, contains less than 50% of the total protein of control serum that has not been treated with the method of the invention. In EXAMPLE V, serum samples treated with the collapsible affinity matrix contained less total protein than on average than before treatment.

Serum Specifically Depleted in Serum Albumin and Immunoglobulins

The invention thus provides a serum specifically depleted in albumin and immunoglobulins. As used herein, the term "specifically depleted" means that the serum sample, after the collapsible affinity matrix is removed, contains a substantial amount of identifiable low abundant protein than control serum that has not been treated with the method of the invention. In EXAMPLE VI, treating human serum with the monoclonal HSA2126NX.012 by the collapsible affinity matrix method resulted in the visualization of 20% more 2-D PAGE protein spots when compared to treatment with Cibacron-blue. Cibacron-blue Sepharose treatment of serum (by the immobilized affinity matrix method) quantitatively removes the serum glycoprotein HC gp-39, as determined by immunoassay, while treatment with the HSA2126NX.012 monoclonal results in >75% recovery of this glycoprotein. In EXAMPLE XIII, more polypeptides remained in the collapsible affinity matrix sample compared to the immobilized matrix sample. Analysis of the most clearly resolved area of the gels calculated 164 polypeptide spots for the collapsible affinity matrix versus 108 polypeptide spots for the immobilized matrix. Due to the microporous nature of the rigid Sepharose beads, that possess an inherent dead volume, low abundant proteins of interest are trapped. By contrast, the collapsible, low void-volume, affinity matrix does not trap low abundant proteins of interest.

The removal of albumin and immunoglobulin, the two most abundant proteins in serum, allows one to load a higher percentage of novel polypeptides that are relevant to a variety of disease states yet are low in abundance and are not detectable using untreated serum and the existing limitations of 2-D gel electrophoresis techniques. The more specific removal of serum albumin is accompanied by the less removal of other proteins, either by trapping or nonspecific binding. The removal of serum albumin and immunoglobulin is particularly important for identification of proteins that have isoelectric points or molecular weights that are similar to these proteins. In the case of an untreated serum sample, potentially novel proteins with diagnostic or therapeutic potential are masked by the overwhelming amount of HSA or Ig on the 2-D gels. The "overloading" of serum albumin and immunoglobulin can also effect the focusing and running of nearby proteins and can cause undesired distortion of the 2-D protein pattern.

Fractionation

The invention provides a method for preparing a liquid sample for protein fractionation. As used herein, the term "protein fractionation" refers to an analytical technique used to separate molecules. Several of the methods of fractionation well-known to those of skill in the art include chromatography, electrophoresis, and isoelectric focussing.

Chromatography is an analytical technique used to separate molecules based on how they tend to cling to or dissolve in various solids, liquids and gases. Many chromatographic methods are known to those of skill in the art. Gel filtration chromatography is used most often to separate proteins by running the solution containing the proteins through a column filled with porous carbohydrate gel beads that traps or slows down smaller molecules but allows larger molecules to slide past. Paper chromatography and thin-layer chromatography separate molecules by taking advantage of their differing solubilities in a mix of solvents. The material to be separated is applied to a special piece of material, and the edge material is put in the solvent mix. The material to be separated travels through the chromatographic material by capillary action and the solvent carries the different molecules at different rates. Ion exchange chromatography is a technique of analytical chemistry used to separate and purify a biological molecule from a mixture, based on the attraction of the charge of the molecule of interest. The mixture, present in a buffer having one ionic property is passed through a column containing a resin of polymers that have fixed charged groups attached to the stationary substance. The molecule of interest stays within the column while much of the rest of the mixture continues through to the end. Then, a buffer having a different ionic property is flushed through the column to detach the molecule from the resin and separate the molecule from the portion of the mixture that has a different charge. Affinity chromatography is a technique of analytical chemistry used to separate and purify a biological molecule from a mixture, based on the attraction of the molecule of interest to a particular ligand that has been previously attached to a solid, inert substance. The mixture is passed through a column containing the ligand attached to the stationary substance, so that the molecule of interest stays within the column while the rest of the mixture continues through to the end. Then, a different chemical is flushed through the column to detach the molecule from the ligand and separate the molecule from the rest of the mixture. High-performance liquid chromatography (HPLC) is a type of column chromatography that uses a combination of several separation techniques to separate substances at higher resolution. Extremely sharp peaks on the elution profile can be produced with high-performance liquid chromatography.

Electrophoresis is a method for separating large molecules (such as DNA fragments or proteins) from a mixture of similar molecules. An electric current is passed through a medium containing the mixture, and each kind of molecule travels through the medium at a different rate, depending on electrical charge and size. Separation is based on these differences. Agarose and acrylamide gels are the media commonly used for electrophoresis of proteins and nucleic acids. Specific electrophoretic methods include Northern blot, Southern blot, and Western blot. Agarose gel electrophoresis is a type of electrophoresis that uses a matrix of highly purified agar to separate large DNA and RNA molecules (generally around 20,000 nucleotides in size). Capillary electrophoresis is a technique for separating compounds; a sample of a compound to be separated is placed in a capillary tube, which is then subjected to a high voltage current that separates chemical components. Disc electrophoresis (short for "discontinuous electrophoresis") is a type of polyacrylamide gel electrophoresis. This electrophoresis method uses gels of two different concentrations of polyacrylamide (a synthetic polymer), the one of lower concentration stacked on top of the one with higher concentration, in order to better resolve bands of whatever is being separated (DNA, RNA, or protein) that would otherwise be very close together.

Isoelectric focusing is a technique used in electrophoresis that separates molecules on the basis of their different isoelectric points.

In one embodiment, method of fractionation is a preparative 2-D gel electrophoresis system, such as that described by Merrick et al. (U.S. Pat. No. 5,534,121, issued Jul. 9, 1996). This method is a single procedure for separation and isolation of preparative amounts of proteins from complex biological preparations. The system includes sized-up isoelectric focusing tube gels and slab gel molds that allow for sample loads of between about 0.5 and 2 mg or greater. Increased protein loads, resolution and electrotransfer allow for subsequent sequencing of separated proteins by conventional methods.

In another embodiment, the method of fractionation is a 2-D PAGE, such as that described by Rabilloud et al. (*Electrophoresis* 15: 1552–1558, 1994). This method includes in-gel sample rehydration of immobilized pH gradient strips to allow larger sample volume, followed by isoelectric focusing in the first dimension and SDS-PAGE in the second dimension. As used herein, the term "High Capacity Two-Dimensional Polyacrylamide Gel Electrophoresis" ("HiCap 2-D PAGE") refers to the use of this method of fractionation on a sample that has been treated to remove high abundant serum proteins. With the removal of abundant proteins, a higher amount of low abundant proteins can be fractionated. For example, HiCap 2-D PAGE of serum permits higher amounts of low abundant proteins to be loaded following the removal of albumin and immunoglobulin. HiCap 2-D PAGE also permits larger sample load due to in-gel sample rehydration (volumes up to 400 $\mu$L) . The combination of abundant protein removal by the collapsible affinity matrix and HiCap 2-D PAGE produces highly reproducible maps of low abundance serum proteins in liquid sample. Following isoelectric focusing in the first dimension, SDS-PAGE in the second dimension and silver stain visualization, computer image analysis allows detection of very small amounts of protein.

HiCap 2-D PAGE can be used in the analysis of disease state serum samples when compared to normal serum. This allows the identification and characterization of a variety of novel markers that may have diagnostic or therapeutic utility. The discovery of novel biochemical serum markers for diagnosis or therapy aids immensely in the management of many diseases. The advantage of HiCap 2-D PAGE mapping is that a large number of distinct unknown serum proteins (~4000), from a single patient sample, can be identified (with respect to isoelectric point and molecular weight) and quantitated at the same time. With the appropriate patient sample set, concentrations of unknown proteins in serum can be correlated to other known clinical measures, such as bone mineral density, and serum and urinary biochemical markers. In this way, clinical utility of a large number of unknown proteins can be evaluated simultaneously. 2-D mapping of low abundance serum proteins requires specific removal of highly abundant proteins, such as human serum albumin and immunoglobulins.

For example, HiCap 2-D PAGE can be used for the discovery of biochemical serum markers for Paget's disease. This method can be applied to the analysis of thirty samples from healthy postmenopausal women at baseline and after three months treatment with an estrogen or selective estrogen receptor modulator. Results showing considerable differences in the 2-D mapping of several polypeptides between the treated and untreated patient samples are described in EXAMPLE XII.

Kit

The materials for use in the assay of the invention are ideally suited for the preparation of a kit. Such a kit may include two or more containers, such as vials, tubes, and the like. Each of the containers contains one of the separate elements to be used in the method. The first container contains a monoclonal antibody capable of immunoprecipitating albumin from serum, to which is bound a first member of a high affinity binding pair. Such a polypeptide affinity reagent may be biotinylated HSA2126NX.012. The second container contains a second member of a high affinity binding pair, for example, avidin, streptavidin, or NEUTRAVIDIN™ (Molecular Probes, Inc., Eugene, Oreg.).

The invention will be further described in the following EXAMPLES, which do not limit the scope of the invention described in the claims.

EXAMPLE I

PRODUCTION OF A MONOCLONAL ANTIBODY THAT CAN IMMUNOPRECIPITATE HUMAN SERUM ALBUMIN

This EXAMPLE provides a description of how the monoclonal antibody HSA2126NX.012 was produced. This antibody is unique in that the antibody can immunoprecipitate albumin from serum. This means that the antibody recognizes an epitope on the HSA molecule that is not blocked by the myriad of serum proteins that are known to bind HSA in serum.

Immunizations. Three BALB/C mice were immunized with Human Serum Albumin (fatty acid free, globulin free, Sigma Chemical Company, St. Louis, Mo.) according to the following protocol. 100 μg antigen emulsified in Complete Freund's Adjuvant was administered subcutaneously at multiple sites. After 3 weeks, each mouse was immunized subcutaneously with 100 μg of antigen in Incomplete Freund's Adjuvant and this schedule continued for three more intervals. The animals were tested for titer. A final intravenous boost of immunogen in phosphate buffered saline was administered to the chosen mouse and three days later the spleen was harvested.

Fusion and screening. Mouse splenic cells were fused with SP2/0 myeloma cells in accordance with standard procedures using polyethylene glycol (PEG). Hybridoma supernatants were initially screened by ELISA. Supernatant antibodies showing reactivity towards the biotinylated HSA antigen (2 μg/mL) on 96-well streptavidin plates (Labsystems) were detected by anti-mouse IgG-peroxidase conjugate (Zymed). Anti-HSA secreting hybridomas were subcloned by limiting dilution. Subcloned hybridomas were adapted to serum-free conditions (HB-Pro; Irvine Scientific) for antibody production. HSA specific monoclonal antibodies were screened a second time for their ability to immunoprecipitate HSA from human serum. The clones capable of immunoprecipitation of human serum albumin were subcloned and isotyped (IsoStrip, Boehringer-Mannheim). The clone, HSA2126NX (IgG2b), was chosen for continuing studies based on the ability to produce large quantities of antibody that efficiently immunoprecipitated albumin from human serum. Further subcloning lead to the choice of HSA2126NX.012. Primary and secondary seedlots were frozen for production scale work.

Screening clones for ability to immunoprecipitate HSA. Various hybridoma culture supernatants were passed over an HSA column to affinity purify anti-HSA monoclonal antibodies. Elution was with 0.1M glycine, pH 3.0. The eluent was concentrated to 100–200 μL for evaluation of HSA immunoprecipitation capability.

Human serum, stripped of endogenous immunoglobulin by previous incubation with protein A and gamma-bind, was incubated overnight at 4° C. with the various anti-HSA antibodies. Gamma-bind was added and incubation took place at 4° C. for 3 hours with rotation. The gamma-bind beads, washed two times with PBS, were then mixed with reducing buffer and boiled. Boiling removed the bound anti-HSA antibody as well as any human serum albumin bound by the specific antibody. This material, run on a sizing gel and stained with Coomaisse blue, displayed either antibody bands only or antibody plus HSA.

Antibody Production. Monoclonal antibody HSA2126NX.012 was produced from hybridoma cultures grown in HB Pro medium (Irvine Scientific, Irvine, Calif.), that is serum free, contains no albumin and is low in total protein content (1 μg/mL). Flasks were incubated at 37° C. with humidity and 5% $CO_2$. IgG quantitation of supernatants from actively growing flask cultures was in the 35–45 μg/mL range. For larger scale production, a CELLMAX® artificial capillary system (Spectrum, Germantown, Md.) was used. Well-established bioreactor culture yields 1–3 mg antibody per mL of supernatant. Eighty mL supernatant can be obtained per week from three harvestings.

Purification of anti-HSA monoclonal antibody. HSA2126NX.012 (ATCC accession No. HB12464) cell culture supernatant was 0.2 μm filtered and run over a Protein A Sepharose (Pharmacia) column. The column was washed with 10 column volumes of phosphate buffered saline (10 mM sodium phosphate, 150 mM sodium chloride, pH 7.0) Bound antibody was eluted with 0.1M glycine, pH 3.0 and neutralized by the addition of (10% by volume) 1.2M Tris, pH 8.5. The purified antibody was dialyzed into 50 mM sodium bicarbonate, pH 8.5. A normal yield was 1 mg of purified antibody per mL of bioreactor supernatant.

EXAMPLE II

BIOTINYLATIONS

Purified anti-HSA monoclonal antibody and recombinant protein A (Scripps Laboratories) were biotinylated in the same manner. Biotinylation was performed with a 20 fold excess of sulfosuccinimidyl-6-(biotinamido) hexanoate (Immunopure® NHS-LC-Biotin, Pierce Chemical Co., Rockford, Ill.) in 50 mM sodium bicarbonate buffer, pH 8.5 at a protein concentration of 3–5 mg/mL. The reaction was carried out for 2 hr at room temperature with rotation. The labeled protein was dialyzed in 5 mM phosphate, 50 mM sodium chloride, pH 7.0 overnight at 4° C. and with a total of two 5 L buffer changes. The biotinylated anti-HSA was concentrated in a Centricon-30 apparatus (Amicon, Inc., Beverly, Mass.) to a final concentration of 6–10 mg/mL. The biotinylated protein A solution was not concentrated.

EXAMPLE III

FORMATION OF "COLLAPSIBLE AFFINITY MATRICES" SPECIFIC FOR HUMAN SERUM ALBUMIN (HSA) AND SERUM IMMUNOGLOBULIN (Ig)

This EXAMPLE provides information on the formation of collapsible affinity matrices specific for human serum albumin and immunoglobulin.

In one test, a biotinylated protein A and avidin collapsible affinity matrix for the removal of serum immunoglobulins was prepared by combining 0.4–0.6 mg biotinylated protein A and 1.2 mg avidin (200 mg/mL avidin in deionized water) per 100 μL of human serum to be treated. This material was vortexed, incubated for 10 minutes (min) and centrifuged at 5000 rpm for one min. The supernatant was discarded and the biotinylated protein A and avidin collapsible affinity matrix pellet was recovered.

In another test, a biotinylated anti-HSA and avidin collapsible affinity matrix for the removal of human serum albumin (HSA) was prepared by combining 10 mg biotinylated anti-HSA monoclonal antibody and 15 mg avidin (200 mg/mL avidin in deionized water) per 100 μL of human serum to be treated. This material was vortexed, incubated for 10 min and centrifuged at 5000 rpm for one min. The supernatant was discarded and the biotinylated anti-HSA and avidin collapsible affinity matrix pellet was recovered. The pellet was washed once with 200 mM NaCl, 5 mM Tris, pH 7.5 to remove any excess avidin.

Removal of Ig and HSA from a human serum sample. The volume of human serum to be treated was added to the biotinylated protein A and avidin pellet, vortexed and incubated 15 min. At this step, immunoglobulins in the serum sample are bound by the biotinylated protein A and avidin collapsible affinity matrix. The treated serum was added to the biotinylated anti-HSA and avidin collapsible affinity matrix pellet and vortexed. The transfer tube was rinsed with 200 mM NaCl, 5 mM Tris, pH 7.5 and this wash was added as well. Incubation was for 1 hr at room temperature with rotation. At this step, HSA in the serum sample was bound by the biotinylated anti-HSA and avidin collapsible affinity matrix. Centrifugation was at 12,000 rpm to allow the collapsible affinity matrices to pellet, thus depleting the serum sample of both HSA and Ig. The supernatant was exchanged against deionized water to remove excess salts and concentrated to less than 100 μL in a Centricon-3 apparatus (Amicon, Inc.). The treated sample was ready to be fractionated without interference by the abundant proteins HSA and Ig.

EXAMPLE IV

HiCap 2-D PROCEDURE

The method of HiCap 2-D PAGE combines the use of a collapsible affinity matrix to remove high abundant proteins from a liquid sample with a modified 2-D PAGE procedure as described by Rabilloud et al., supra. First, the HSA and Ig depleted serum samples were adjusted to a final volume of 400 μL with rehydration buffer (8M urea, 4% CHAPS, 0.1% Pharmalytes 3–10, 0.2% Triton X-100, 0.1% taurodeoxycholate and 10 mM DTT). The entire 400 μL sample was used to rehydrate a 3 mm×18 cm immobilized pH gradient (IPG) strip (3.3% total acrylamide/2.7% piperazine diacrylyl as crosslinker; Immobiline concentrations as per published recipes). Rehydration was overnight at room temperature in a rehydration chamber. For the first dimension, the rehydrated IPG strips were focused at 15° C. and an upper voltage limit of 6 kV for greater than 100 kV-hr. The focused IPG strips were then reduced with DTT and alkylated with iodoacetamide while also being equilibrated with SDS (equilibration buffer base: 30% glycerol, 6M urea, 2.5% SDS, 0.15M BisTris, 0.1M HCl and bromophenol blue). For the second dimension, the equilibrated IPG strip was sealed to a 3% stacking/14% resolving gel (Prosieve 50; FMC BioProducts, Rockland, Me.) with dimensions of 20×20×1.5 cm. Electrophoresis was at 4° C. in SDS/Tricine buffer until the tracking dye reached the bottom of the gel. Upon completion of electrophoresis, the PAGE gels were fixed and silver stained for polypeptide visualization. Dried gels were scanned, digitized and analyzed using the GELLAB II+ software package (Scanalytics; Billerica, Mass.).

EXAMPLE V

STATISTICS ON THE REMOVAL OF Ig AND HSA USING THIS CLARIFICATION TECHNIQUE

Twelve serum samples were evaluated for total protein concentration pre-removal and post-removal of HSA and Ig. The protein concentrations were assayed using micro BCA (Pierce). The results from the twelve samples were very consistent and showed a mean total protein post-treatment= 18.5±2.6 mg/mL, compared with a mean total protein pretreatment=65.3±4.0 mg/mL.

Therefore, 46.8 mg of immunoglobulin and human serum albumin was removed with the collapsible affinity matrix clarification technique. The remaining protein (28% of initial) contains low abundant serum proteins, that can then be analyzed by further fractionation methods, for example, 2-D PAGE.

EXAMPLE VI

SAMPLE TREATMENT FOR REMOVAL OF HSA AND Ig

Figure 1B:
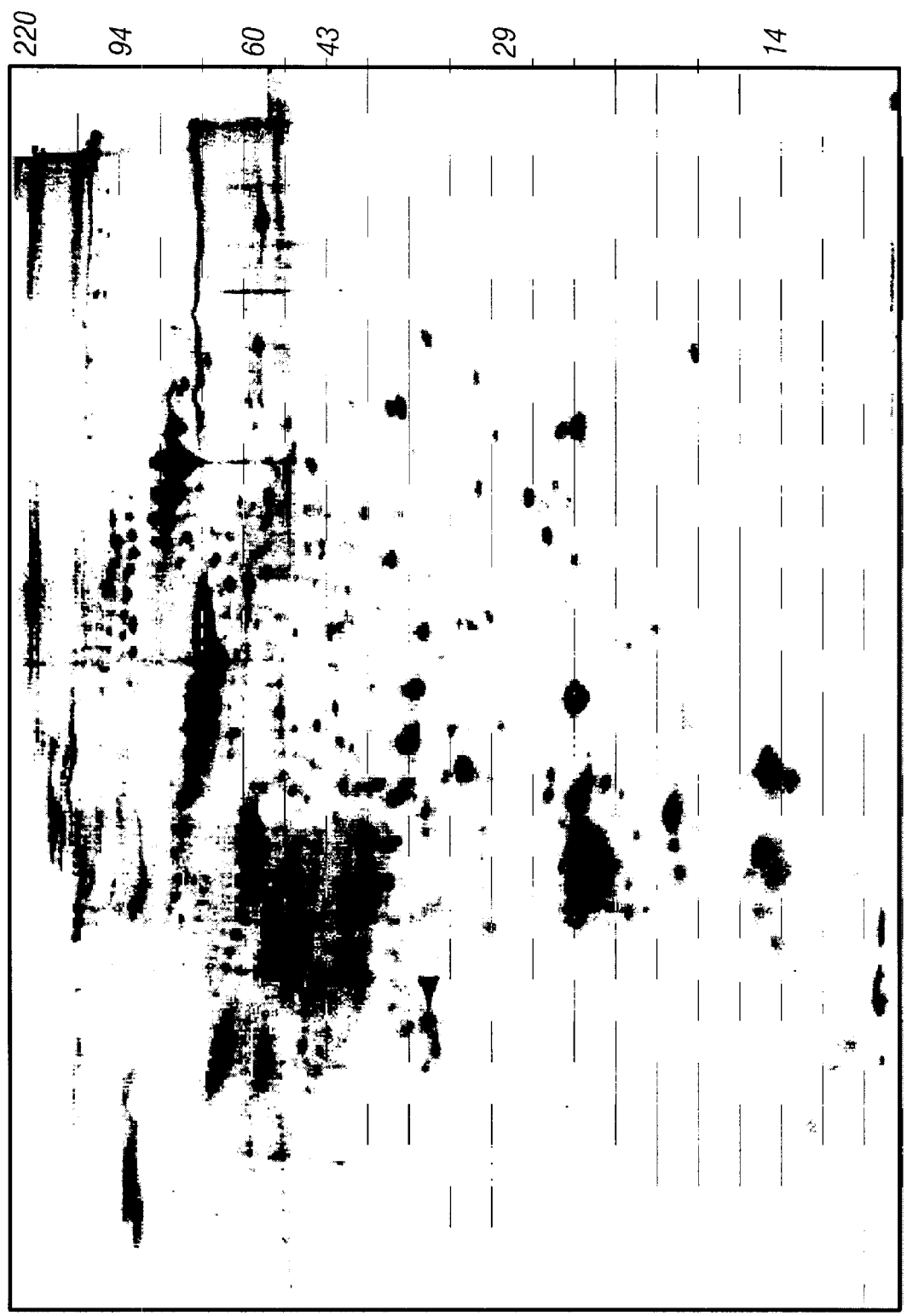
Figure 1C:

This EXAMPLE demonstrates a preparation of a serum sample that is substantial depleted in serum albumin and immunoglobulin. Human serum samples were treated with a monoclonal antibody specific for HSA (biotinylated anti-HSA, HSA2126NX.012) and avidin or Cibacron-blue dye. Both treated samples were subsequently incubated with gamma-bind protein A to remove immunoglobulin. The removal of serum albumin and immunoglobulin was done to enable larger sample loads and higher quality 2-D PAGE gels of human serum. FIGS. 1 and 2 demonstrate the effectiveness of the specific removal by the monoclonal antibody and compare this method of treatment to an alternative method, using immobilized Cibacron-blue dye. FIG. 1 shows the 2-D maps (performed using standard ampholine-based IEF) for volume normalized (5 μL) human serum samples that are: untreated (FIG. 1A); monoclonal treated (FIG. 1B) and treated with immobilized Cibacron-blue (FIG. 1C).

Figure 2A:
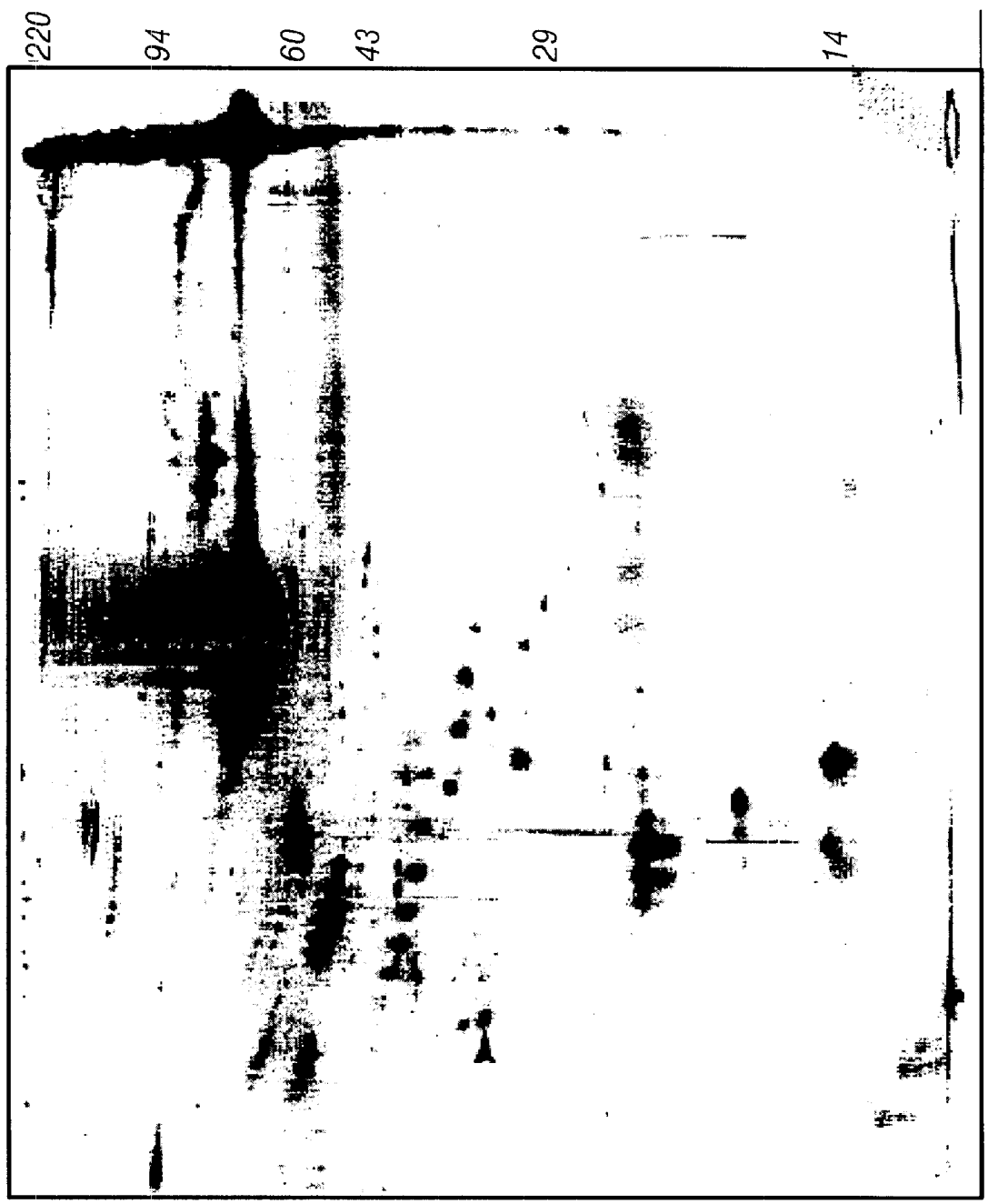
FIGS. 2A–C are a 2-D PAGE of 250 $\mu$g total protein from human serum, where the serum is A) untreated; B) treated with anti-HSA monoclonal HSA2126NX.012; and C) treated with Cibacron-blue.
Figure 2B:
Figure 2C:
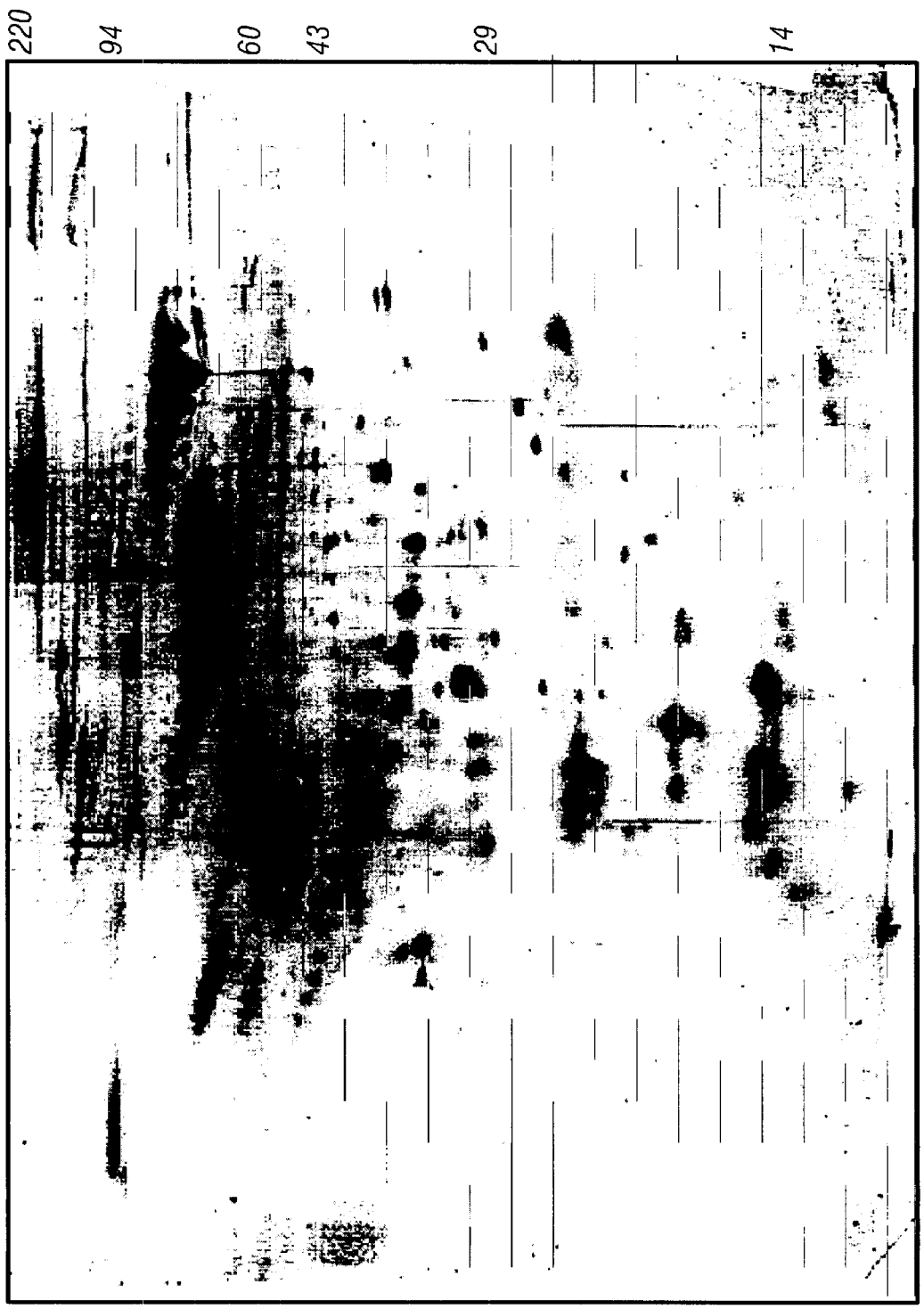
Figure 3:
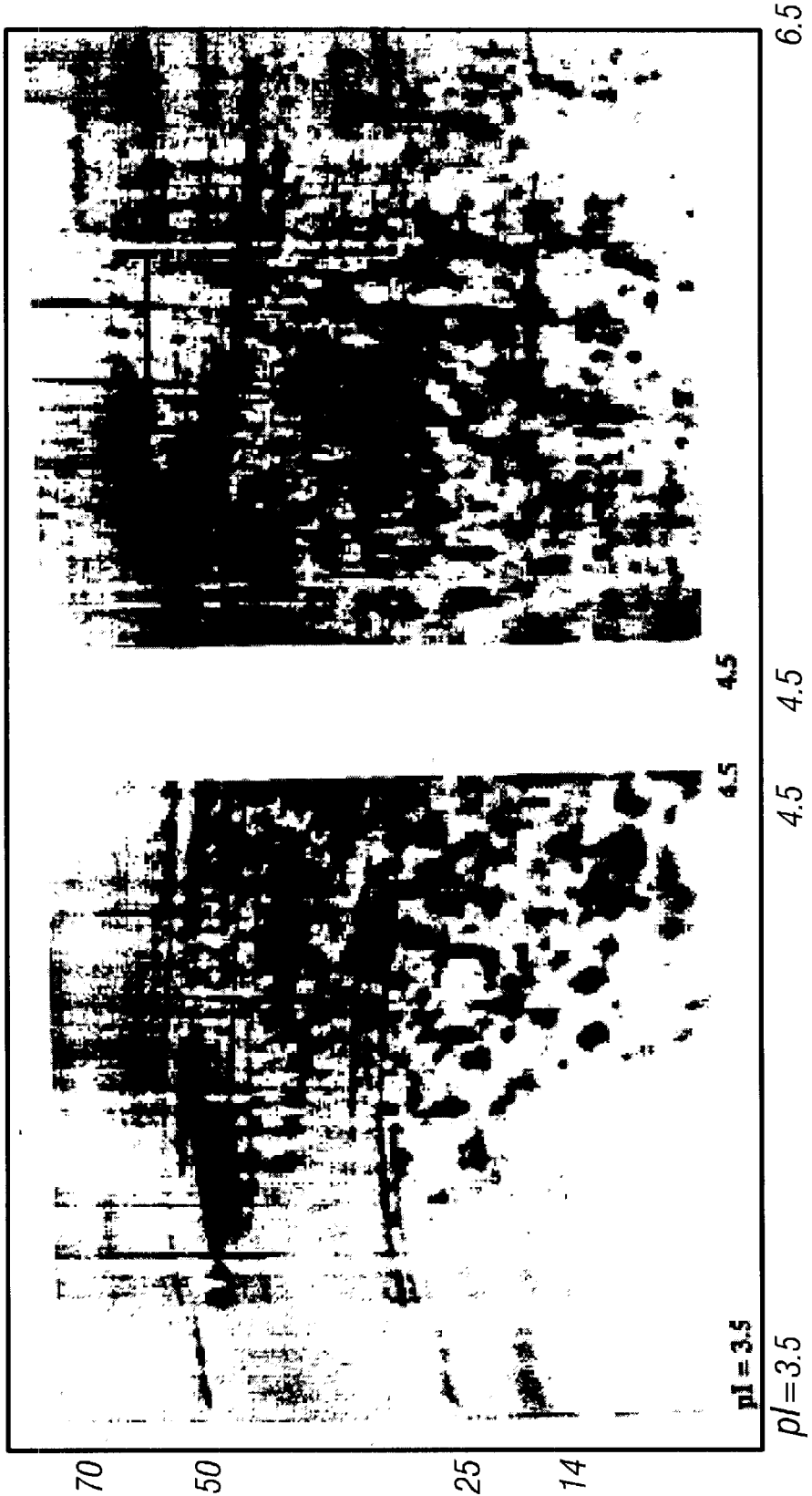
FIG. 3 is a 2-D PAGE polypeptide map of 100 μL human serum treated for the removal of HSA and Ig. The 100 μL human serum was treated (albumin and Ig removed) and analyzed according to the methods described in EXAMPLES III and IV. The entire map (pH 3.5–8.0) is a composite of three separate 2-D gels spanning three different pH regions (3.5–5.0, 4.5–6.5 and 6.0–8.0). When 100 μL of treated human serum is analyzed, approximately 4000 polypeptide spots can be detected. The greatest number of protein spots previously reported to be detected in serum was 2500.
Figure 4A:
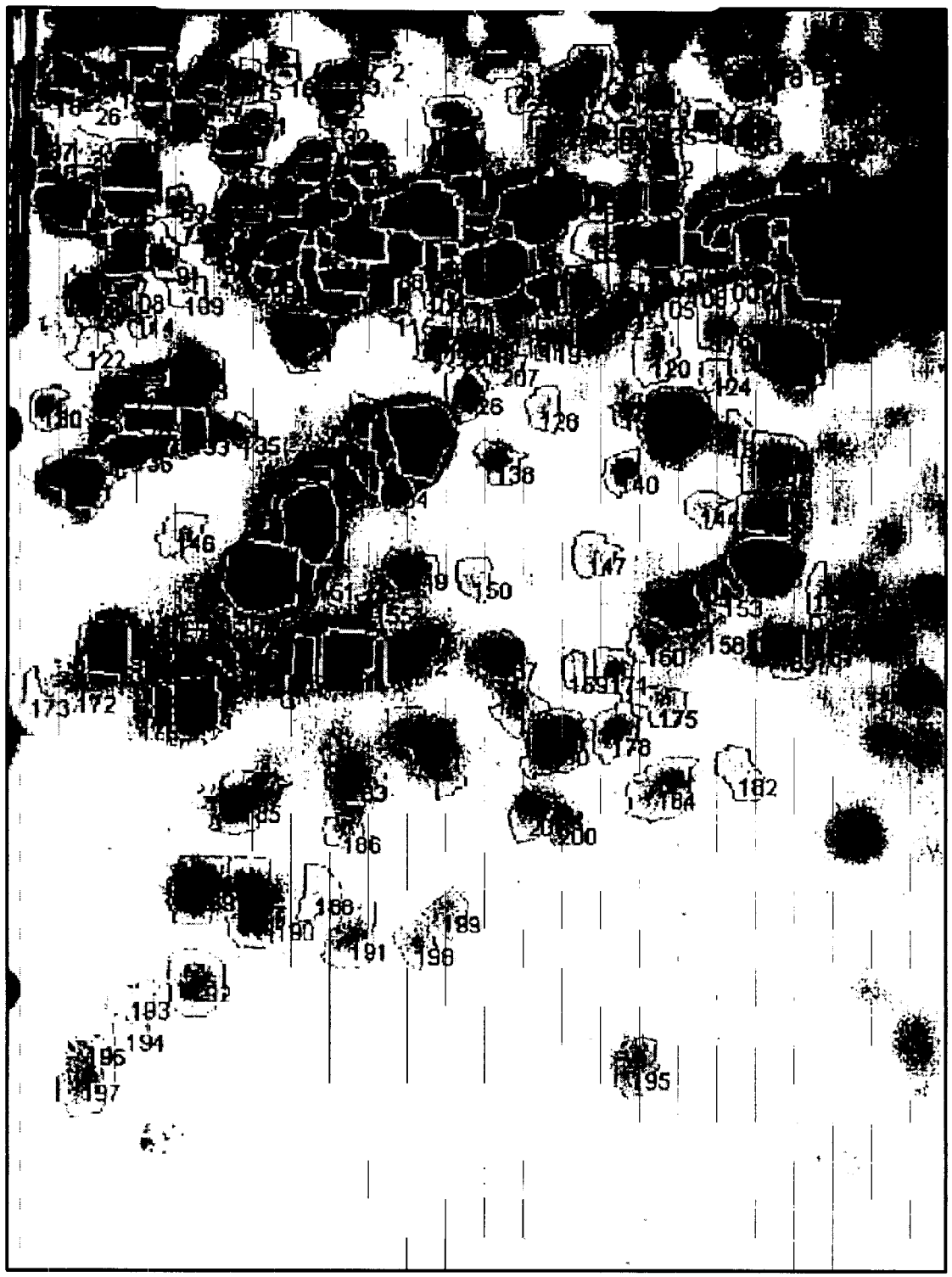
FIGS. 4A and B are a duplicate of 2-D PAGE gels showing gel-to-gel spatial reproducibility. Two identical 100 μL human serum samples were treated and analyzed according to the methods described in EXAMPLES III and IV. Within the region of interest, there were 212 spots detected in gel 1, as shown in FIG. 4A, and 232 spots detected in gel 2, as shown in FIG. 4B.
Figure 4B:
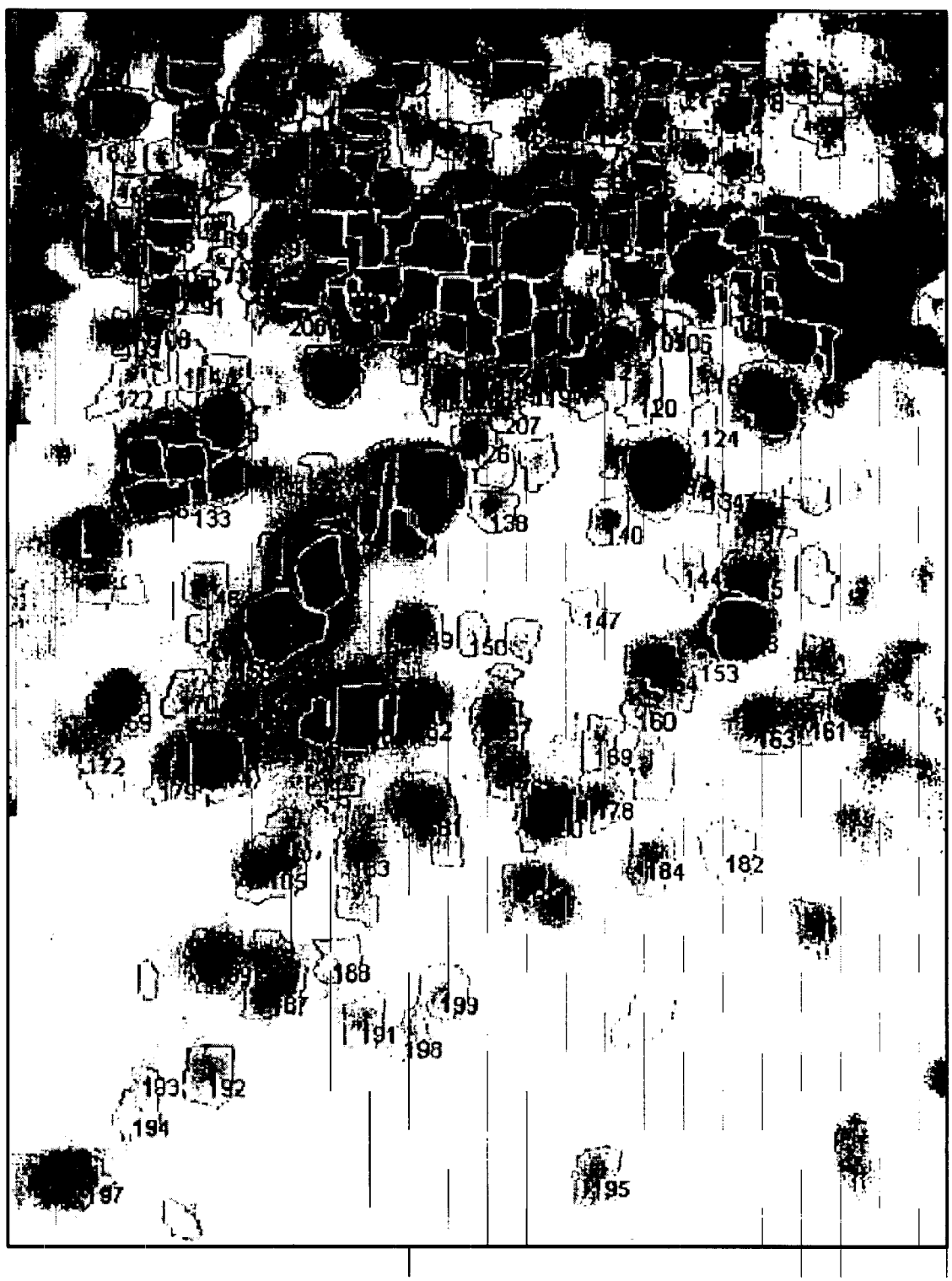
Figure 5:
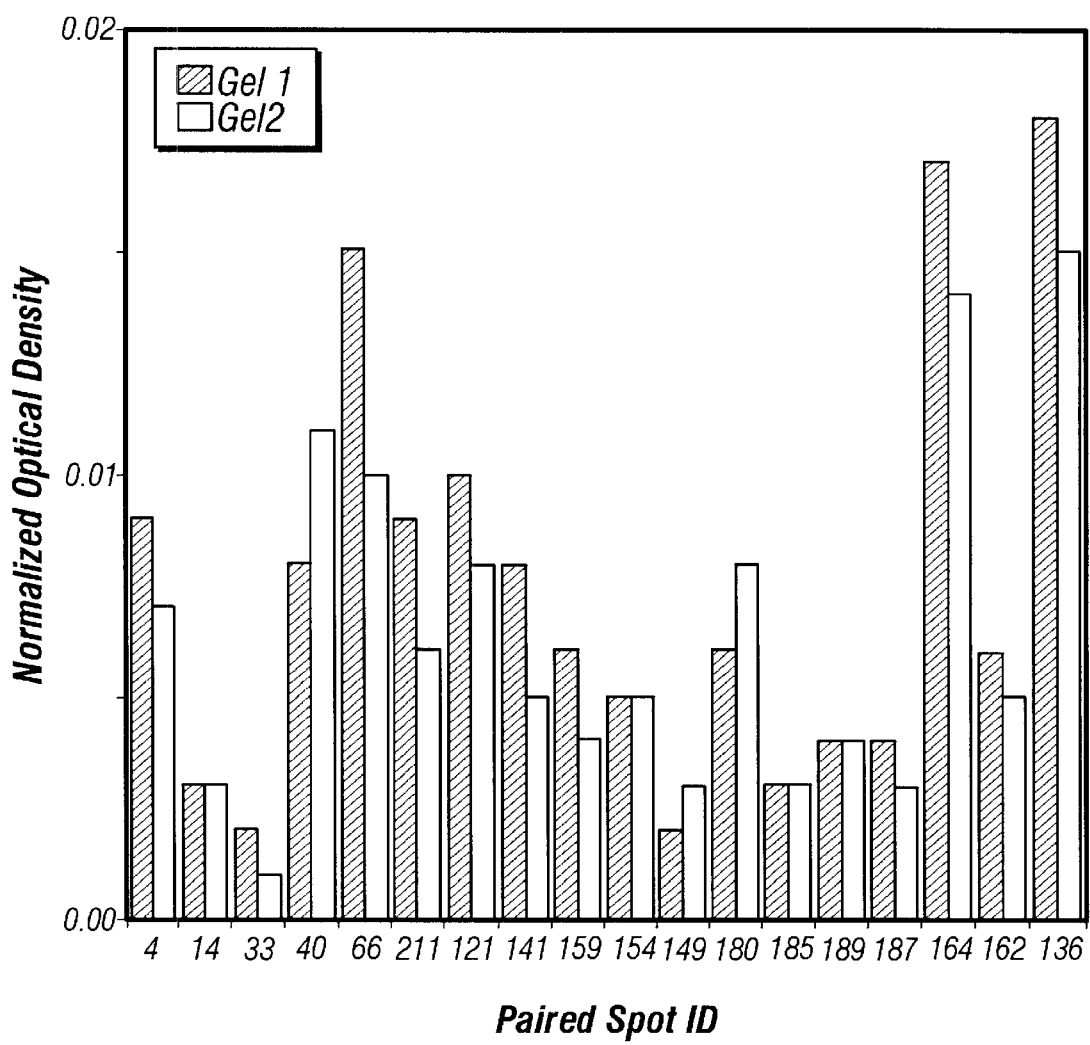
FIG. 5 is a bar graph showing gel-to-gel spatial reproducibility.

The purpose of showing the volume normalized maps is to demonstrate the increased quality of the gel image by removal of HSA and Ig. Also, comparing maps 1B and 1C shows the increased specificity of the monoclonal treatment versus Cibacron-blue. Gel 1B has 1200 polypeptide spots compared to 1000 spots on Gel 1C. Treating human serum with the monoclonal HSA2126NX.012 resulted in 20% more spots when compared to treatment with Cibacron-blue, indicating a significant increase in specificity. Another indication of increased specificity comes from the observation that Cibacron-blue treatment of serum quantitatively removes the serum glycoprotein, HC gp-39, (as determined by immunoassay) while treatment with the HSA2126NX.012 monoclonal results in >75% recovery. FIG. 2 shows the 2-D maps that are normalized for the total amount of protein load (250 μg) after: no treatment (FIG. 2A); monoclonal treatment (FIG. 2B) and Cibacron-blue treatment (FIG. 2C). The total protein normalized 2-D maps reveal the large increase of information obtained by removing HSA and Ig when the analytical technique is sensitive to the total protein load. When HSA and Ig were removed from the sample, the number of polypeptide spots detected increased approximately two-fold (FIG. 2A versus FIGS. 2B and 2C).

From the above results, it becomes clear that the specific removal of serum albumin and immunoglobulin can greatly enhance the information obtained from analytical 2-D PAGE gels.

EXAMPLE VII

A COMPARISON OF 2-D ELECTROPHORESIS USING UNTREATED SERUM, MONOCLONAL ANTI-HSA ANTIBODY TREATMENT, AND CIBACRON-BLUE TREATMENT, USING VOLUME NORMALIZED SAMPLES

The purpose of this EXAMPLE is to show the improved performance of the method of the invention over existing methods. Human serum samples were treated with a monoclonal antibody specific for HSA (biotinylated anti-HSA, HSA2126NX.012) and avidin or Cibacron-blue dye. Both treated samples were subsequently incubated with gamma-bind protein A to remove the immunoglobulin. The removal of albumin and immunoglobulin was done to enable larger loads of the less abundant serum proteins and higher quality 2-D PAGE gels of human serum.

FIG. 1 demonstrates the effectiveness of the specific HSA removal by the monoclonal antibody treatment and compares this method of treatment to an alternate method, using immobilized Cibacron-blue dye. FIG. 1 shows the 2-D maps for volume normalized (5 μL) human serum samples that are: untreated (FIG. 1A); treated with an anti-HSA monoclonal (FIG. 1B) and treated with immoblilized Cibacron-blue (FIG. 1C).

The purpose of showing the volume normalized maps is to demonstrate the increased quality of the gel image by removal of HSA and Ig. Also, comparing the maps in gels 1B and 1C shows the increased specificity of the monoclonal treatment versus Cibacron-blue. Gel 1B has 1200 polypeptide spots compared to 1000 spots on Gel 1C. Treating human serum with the monoclonal HSA2126NX.012 resulted in 20% more protein spots when compared to treatment with Cibacron-blue, indicating a significant increase in specificity.

Therefore, this method of the invention allowed the detection of proteins that would otherwise not have been resolved using established procedures that nonspecifically bind protein, as does Cibacron-blue.

EXAMPLE VIII

A COMPARISON OF 2-D ELECTROPHORESIS USING UNTREATED SERUM, MONOCLONAL ANTI-HSA ANTIBODY TREATMENT, AND CIBACRON-BLUE TREATMENT, USING SAMPLES NORMALIZED FOR TOTAL PROTEIN LOAD

Human serum samples were treated with a biotinylated monoclonal antibody specific for HSA (HSA2126NX.012) and avidin, or Cibacron-blue dye. Both treated samples were subsequently incubated with gamma-bind protein A to remove the immunoglobulin. The removal of albumin and immunoglobulin was done to enable larger loads of the less abundant serum proteins and higher quality 2-D PAGE gels of human serum. FIG. 2 demonstrates the effectiveness of the specific HSA removal by the monoclonal antibody treatment and compares this method of treatment to an alternate method, using immobilized Cibacron-blue dye. FIG. 2 shows the 2-D maps that are normalized for the total amount of protein load (250 μg) after: no treatment (FIG. 2A), treatment with an anti-HSA monoclonal (FIG. 2B) and Cibacron-blue treatment (FIG. 2C). The total protein normalized 2-D maps reveal the large increase of information obtained by removing HSA and Ig when the analytical technique is sensitive to the total protein load. If the albumin and Ig are removed from the sample, the number of polypeptide spots detected increases approximately two-fold (FIG. 2A versus FIGS. 2B and 2C).

Thus, the specific removal of serum albumin and immunoglobulin can greatly enhance the information obtained from analytical 2-D PAGE gels.

EXAMPLE IX

NONSPECIFIC REMOVAL OF GLYCOPROTEIN, HC gp-39 FROM HUMAN SERUM BY CIBACRON-BLUE, BUT NOT MONOCLONAL ANTIBODY

Another indication of increased specificity with the monoclonal antibody method comes from the observation that Cibacron-blue treatment of serum quantitatively removed the serum glycoprotein, HC gp-39 (as determined by immunoassay), while treatment with the anti-HSA specific antibody, HSA2126NX.012, resulted in >75% recovery. This experiment demonstrates the advantage of a specific HSA removal method over a non-specific method.

EXAMPLE X

SPECIFIC HSA REMOVAL BY MONOCLONAL ANTIBODY ALLOWS ANALYSIS OF HSA-BOUND PROTEINS

The purpose of this EXAMPLE is to show the usefulness of specifically immunoprecipitating albumin from serum using the monoclonal antibody HSA2126NX.012. HSA-associated proteins is precipitated from serum by the addition of biotinylated HSA2126NX.012 with streptavidin or avidin.

The pelleted precipitate, containing HSA, is then boiled and analyzed by 1-D or 2-D gel electrophoresis, providing valuable information about HSA-bound proteins. Analysis of the HSA-bound proteins from individuals with various disease states assists in the characterization of the diseases.

The benefits of using the anti-HSA specific monoclonal antibody, rather than other methods, lie in the anti-HSA specific monoclonal antibody specificity. This EXAMPLE shows that the proteins being analyzed are associated with HSA versus being nonspecifically pulled down or trapped in the void space of a slurry matrix.

EXAMPLE XI

MONKEY SERUM ALBUMIN REMOVAL USING THE ANTI-HSA MONOCLONAL ANTIBODY

The anti-HSA antibody, HSA2126NX.012, was evaluated for the ability to efficiently immunoprecipitate albumin from monkey serum. Due to the homology between human and monkey serum albumins, the monoclonal was able to successfully remove the monkey serum albumin. This MSA (monkey serum albumin) removal is a beneficial step in the gel electrophoresis analysis of monkey serum proteins in various disease models or drug treatment analysis.

This depletion of albumin can be performed with any number of mammalian species after the production of a specific monoclonal antibody that recognizes that particular albumin in the respective serum.

EXAMPLE XII

CLINICAL RESULTS

One of the strategies for applying HiCap 2-D PAGE to the discovery of disease related serum proteins is to perform exhaustive analysis on patient samples in which large changes in disease related proteins are expected. For instance, one would expect bone resorption markers to be greatly amplified in Paget's disease patients and people suffering from hyperparathyroid. TABLE 1 shows several examples of some polypeptide species that are up-regulated in a Pagetic sample when compared to an age-matched normal sample.

TABLE I

Serum Proteins Increased in Concentration in Pagetic Patient Versus Normal

| Spot ID | Approximate concentration in Pagetic Sample | Fold change from normal |
| --- | --- | --- |
| 118 | 200 ng/mL | 5 |
| 224 | 100 ng/mL | 6 |
| 192 | 300 ng/mL | 4 |

TABLE I-continued

Serum Proteins Increased in Concentration in
Pagetic Patient Versus Normal

| Spot ID | Approximate concentration in Pagetic Sample | Fold change from normal |
| --- | --- | --- |
| 1133 | 100 ng/mL | >5 |
| 136 | 750 ng/mL | 10 |

Figure 6A:
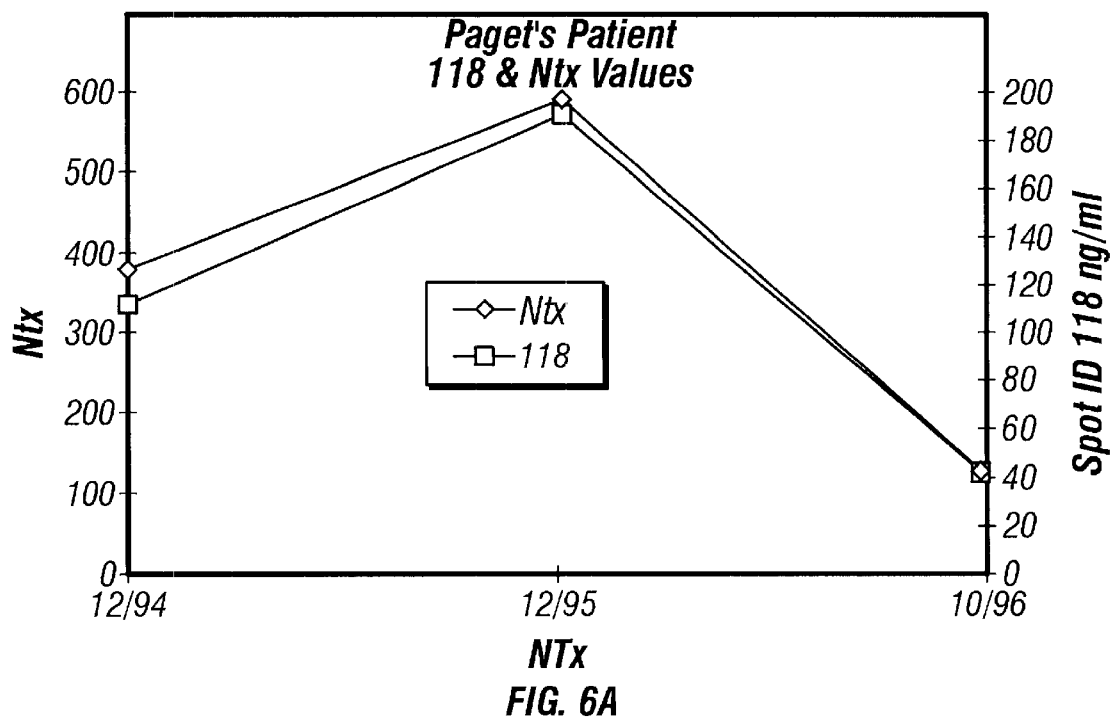
FIGS. 6A and B are a summary of the preliminary results from analysis of patient samples.
Figure 6B:
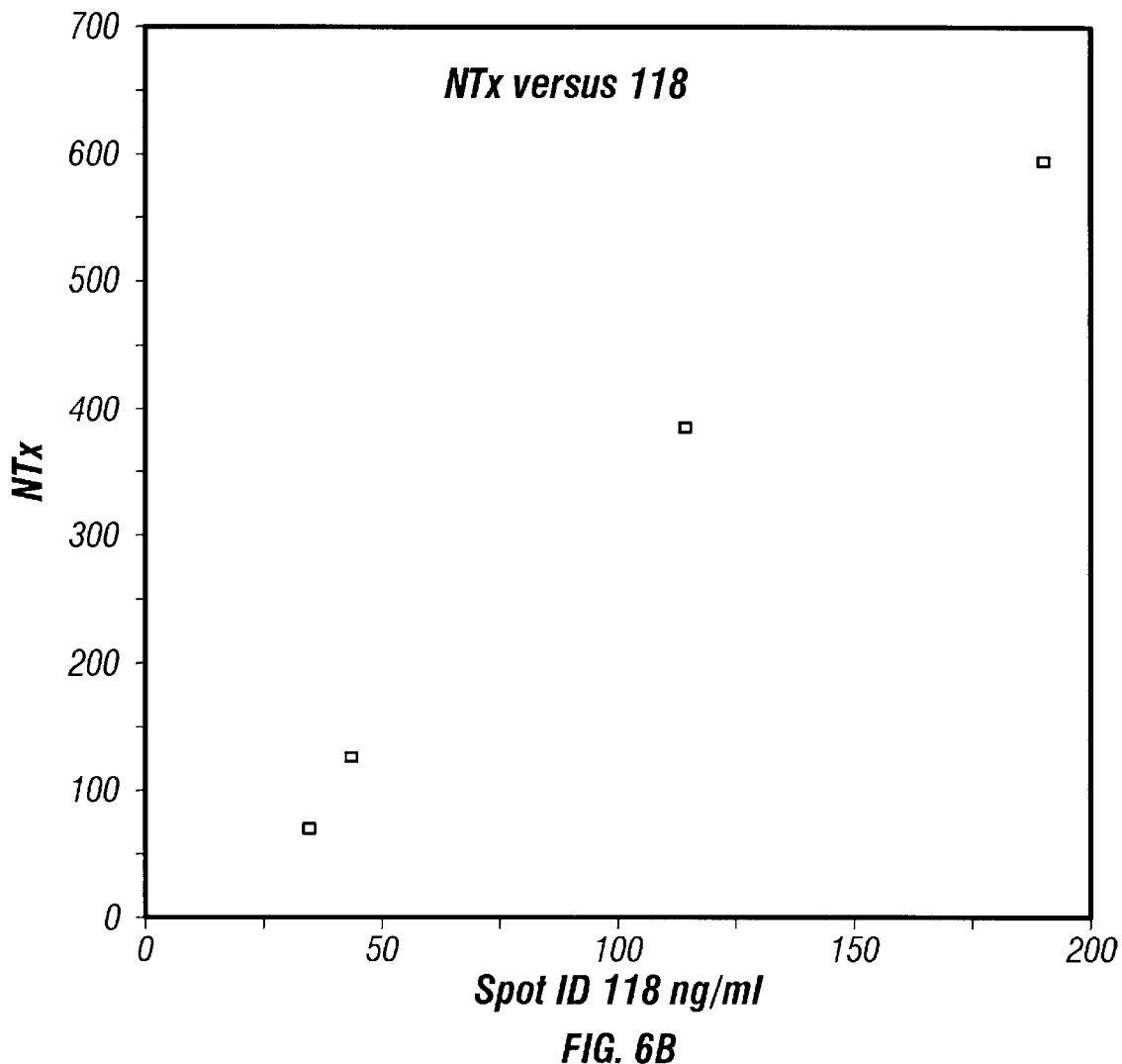
FIG. 6B shows how the spot ID 118 concentration and NTx concentration correlate with one another.

A key element in identifying potential disease related proteins is their correlation with already existing diagnostics. For example, BMD and NTx measurements could be used (with matching serum samples) to identify proteins associated with bone metabolism. This concept is demonstrated with polypeptide Spot ID 118, that follows the disease progression of a Pagetic patient, as determined by NTx values (FIGS. 6A). 6B shows how the spot ID 118 concentration and NTx concentration in serum correlate with one another.

EXAMPLE XIII

A COMPARISON OF THE COLLAPSIBLE AFFINITY MATRIX WITH IMMOBILIZED SEPHAROSE MATRIX FOR SPECIFIC REMOVAL OF HSA AND Ig FROM SERUM

Two aliquots of a serum sample were treated with our biotinylated anti-HSA monoclonal antibody HSA2126NX.012 and biotinylated protein A. The difference between the two samples was in the removal step. To one aliquot was added a rigid streptavidin-Sepharose matrix (Ultralink Immobilized Streptavidin on 3M Emphage Biosupport Medium; Pierce) and to the other sample was added soluble avidin (Scripps Labs; La Jolla, Calif.) to form a collapsible matrix. After 1 hr incubation with mixing, the matrices were separated from the solution by centrifugation. The resulting solution contained serum proteins, but was highly depleted of HSA and Ig. This material was analyzed by a modified 2-D PAGE procedure described by Rabilloud et al., supra.

Figure 7A:
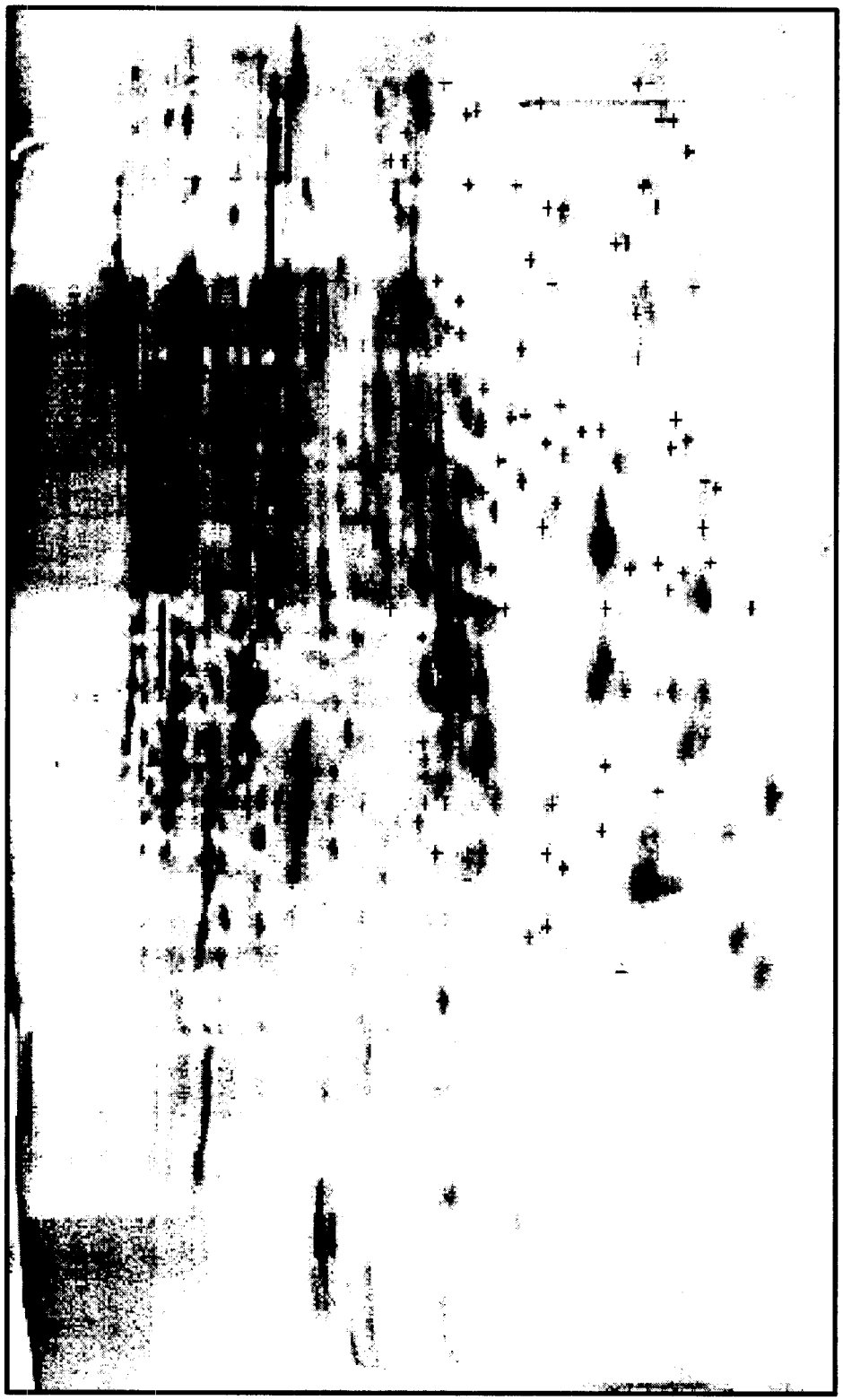
FIGS. 7A and B are a duplicate of 2-D PAGE gels showing that more polypeptides are present in a sample prepared using the collapsible affinity matrix than using an immobilized matrix (a rigid streptavidin-Sepharose matrix, ULTRALINK IMMOBILIZED STREPTAVIDIN™ on 3M EMPHAGE BIOSUPPORT MEDIUM™; Pierce).
Figure 7B:
FIG. 7B is an immobilized matrix sample.

Visualization of the gels clearly showed more polypeptides in the collapsible affinity matrix sample (FIG. 7A) versus the immobilized matrix sample (FIG. 7B). Analysis of the most clearly resolved area of the gels using GELLAB II+ software calculated 164 polypeptide spots for the collapsible affinity matrix versus 108 polypeptide spots for the immobilized matrix. Due to the microporous nature of the rigid Sepharose beads, that possess an inherent dead volume, low abundant proteins of interest are trapped. By contrast, the collapsible, low void-volume, affinity matrix does not trap low abundant proteins of interest.

The advantage is that the dead volume will "collapse" upon centrifugation and hence yield a superior recovery of serum proteins.

EXAMPLE XIV

HiCap 2-D PAGE ASSAY

The following HiCap 2-D procedure is a modification of the method described by Rabilloud et al. (*Electrophoresis* 15: 1552–1558, 1994).

1. Serum samples were treated with the collapsible affinity matrix (as per EXAMPLE III) for removal of HSA and immunoglobulin.

2. The HSA and Ig depleted serum samples were adjusted to a final volume of 400 μL with rehydration buffer (8M urea, 4% CHAPS, 0.1% Pharmalytes 3–10, 0.2% Triton X-100, 0.1% taurodeoxycholate and 10 mM DTT). The entire 400 μL sample was used to rehydrate a 3 mm×18 cm immobilized pH gradient (IPG) strip (3.3% total acrylamide/2.7% piperazine diacrylyl as crosslinker; Immobiline concentrations as per published recipes). Rehydration was overnight at room temperature in a replica of a rehydration chamber described by Rabilloud et al.

3. For the first dimension, the rehydrated IPG strips were focused at 15° C. and an upper voltage limit of 6 kV for greater than 100 kV-hr.

4. The focused IPG strips were then reduced with DTT and alkylated with Iodoacetamide while also being equilibrated with SDS (Equilibration buffer base: 30% glycerol, 6M urea, 2.5% SDS, 0.15M BisTris, 0.1M HCl and bromophenol blue).

5. For the second dimension, the equilibrated IPG strip was sealed to a 3% stacking/14% resolving gel (Prosieve 50; FMC BioProducts, Rockland, Me.) with dimensions of 20×20×1.5 cm. Electrophoresis was at 4° C. in SDS/Tricine buffer until the tracking dye reached the bottom of the gel.

6. Upon completion of electrophoresis, the PAGE gels were fixed and silver stained by the method of Rabilloud (*Electrophoresis* 13: 429–439, 1992) for polypeptide visualization.

7. Dried gels were scanned, digitized and analyzed using the GELLAB II+ software package (Scanalytics; Billerica, Mass.).

8. Molecular weights and pIs for individual protein spots were determined by calibration curves generated by using known serum proteins as internal standards.

9. Protein concentration for individual spots was approximated as follows: the total protein concentration loaded onto the first dimension (determined by BCA) was divided by the integrated optical density (OD) of all spots on the gel to give an average protein concentration per unit OD or Average Staining Unit (ASU); using the ASU, several spots of different intensities were selected and used to construct a calibration curve for estimating the concentration of all protein spots in the gel.

The subject cultures (for HSA2126NX.012) are deposited under conditions that assure that access to the cultures will be available during the pendency of the patent application disclosing them to one determined by the Commissioner of Patents and Trademarks to be entitled thereto under 37 C.F.R. §1.14 and 35 U.S.C. §122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

It is to be understood that while the invention has been described in conjunction with the detailed description thereof, the foregoing description is intended to illustrate and not limit the scope of the invention. Other aspects, advantages, and modifications can be made without departing from the spirit of the invention. Accordingly, the invention is limited only by the following claims.

What is claimed:

1. A monoclonal antibody, wherein the monoclonal antibody is HSA2126NX.012 having ATCC accession No. HB12464.

2. The monoclonal antibody of claim 1, wherein the antibody is biotinylated.

3. A host cell comprising monoclonal antibody HSA2126NX.012, ATCC accession No. HB12464.

4. A kit comprising a first container and a second container, wherein the first container comprises a monoclonal antibody HSA2126NX.012, ATCC accession No. HB12464 and the second container comprises a vial or a tube.

5. An isolated antibody, wherein the antibody has the binding specificity of monoclonal antibody HSA2126NX.012, ATCC accession No. HB12464, wherein the antibody comprises monoclonal antibody HSA2126NX.012 having ATCC accession No. HB12464.

6. A kit comprising a first container and a second container, wherein the first container comprises a monoclonal antibody HSA2126NX.012, ATCC accession No. HB12464, and the second container comprises a second member of a high affinity binding pair.

7. The kit of claim 6, wherein the monoclonal antibody comprises a first member of a high affinity binding pair.

8. The kit of claim 7, wherein the first member of a high affinity binding pair comprises biotin.

9. The kit of claim 6, wherein the second member of a high affinity binding pair is selected from the group consisting of avidin, streptavidin and NEUTRAVIDIN™.

* * * * *